(12) United States Patent
Sayger et al.

(10) Patent No.: US 11,896,236 B2
(45) Date of Patent: Feb. 13, 2024

(54) SURGICAL SAW BLADE

(71) Applicant: CROSSROADS EXTREMITY SYSTEMS, LLC, Memphis, TN (US)

(72) Inventors: Daniel Sayger, Hernando, MS (US); Michael Chad Hollis, Collierville, TN (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 226 days.

(21) Appl. No.: 17/411,783

(22) Filed: Aug. 25, 2021

(65) Prior Publication Data

US 2022/0061855 A1 Mar. 3, 2022

Related U.S. Application Data

(60) Provisional application No. 63/070,479, filed on Aug. 26, 2020.

(51) Int. Cl.
*A61B 17/14* (2006.01)
*A61B 17/16* (2006.01)
*A61B 90/00* (2016.01)

(52) U.S. Cl.
CPC ............ *A61B 17/142* (2016.11); *A61B 17/14* (2013.01); *A61B 17/147* (2016.11); *A61B 17/1659* (2013.01); *A61B 17/1666* (2013.01); *A61B 17/1675* (2013.01); *A61B 2090/0807* (2016.02)

(58) Field of Classification Search
CPC ... A61B 17/14; A61B 17/142; A61B 17/1659; A61B 17/1666; A61B 17/1675
See application file for complete search history.

(56) References Cited

U.S. PATENT DOCUMENTS

| | | | |
|---|---|---|---|
| 2,984,892 A * | 5/1961 | Oxford | B23D 71/00 407/29.1 |
| 4,872,452 A | 10/1989 | Axelson | |
| 5,122,142 A | 6/1992 | Pascaloff | |
| 5,306,285 A | 4/1994 | Miller et al. | |
| D361,029 S | 8/1995 | Goris | |
| 5,725,531 A * | 3/1998 | Shapiro | A61B 17/1686 606/85 |
| D503,800 S | 4/2005 | Ebner | |
| D525,707 S | 7/2006 | Kuellmer et al. | |
| D572,821 S | 7/2008 | Burgard | |
| 8,448,887 B2 * | 5/2013 | Green | A47J 43/25 241/168 |
| 8,617,164 B2 | 12/2013 | Nelson et al. | |
| 9,005,203 B2 | 4/2015 | Nelson et al. | |
| 9,033,986 B2 | 5/2015 | Nelson et al. | |

(Continued)

*Primary Examiner* — Nicholas W Woodall
(74) *Attorney, Agent, or Firm* — BakerHostetler

(57) ABSTRACT

A surgical saw blade is disclosed for improved resection and cutting of tissue. The surgical saw blade may include a front side, an opposite back side, a top side, an opposite bottom side, a right side, and an opposite left side. The surgical saw blade may further include a cutting tooth extending from the back side and having a cutting edge oriented toward one of the right side and the left side, the cutting tooth associated with an aperture through the saw blade between the front and back sides. The back side may be a single direction cutting side and the front, top, bottom, right, and left sides may be non-cutting sides. The surgical saw blade may further include a saw connection feature near the bottom side.

20 Claims, 13 Drawing Sheets

(56) References Cited

U.S. PATENT DOCUMENTS

| | | |
|---|---|---|
| D742,002 S | 10/2015 | Fisher et al. |
| 9,168,600 B2 | 10/2015 | Rugar |
| 9,198,675 B2 | 12/2015 | Nelson et al. |
| 10,485,559 B2 | 11/2019 | Del et al. |
| 2011/0270256 A1 | 11/2011 | Nelson et al. |
| 2015/0360306 A1* | 12/2015 | Reisler .................. B23D 67/04 407/29.15 |
| 2020/0046377 A1 | 2/2020 | Woodard et al. |

* cited by examiner

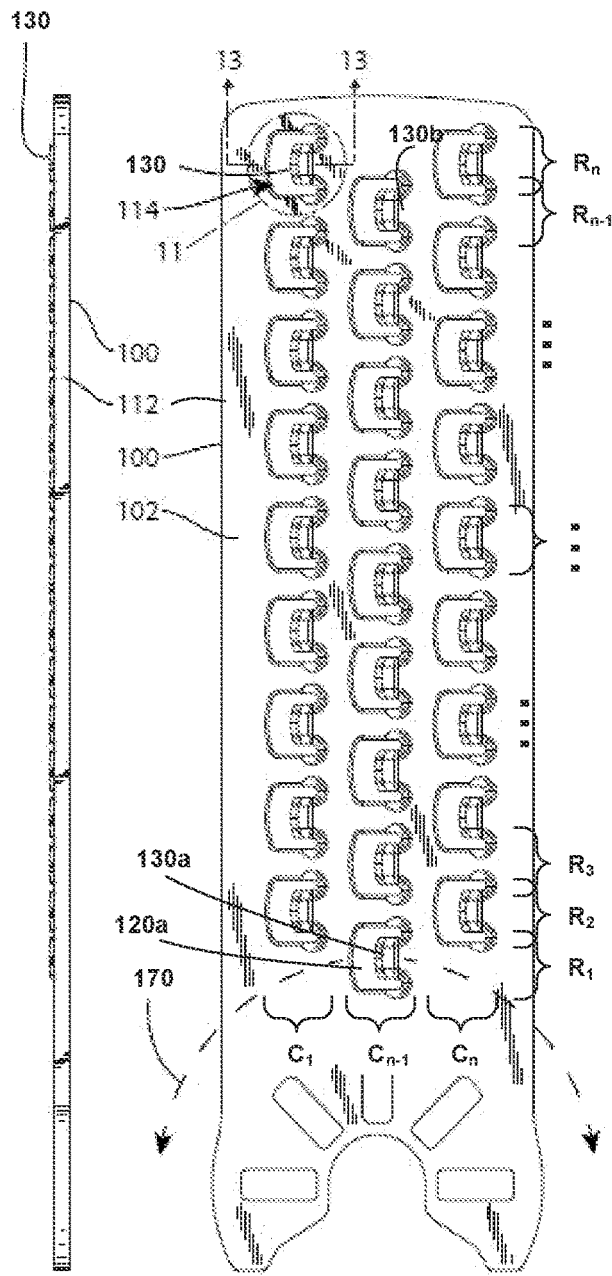

SURGICAL SAW BLADE

CROSS-REFERENCE TO RELATED APPLICATIONS

This application claims the benefit of U.S. Provisional Application No. 63/070,479, filed Aug. 26, 2020, entitled "SURGICAL SAW BLADES" which is hereby incorporated by reference in its entirety.

TECHNICAL FIELD

The present disclosure relates to surgical saw blades. More specifically, the present disclosure relates to surgical saw blades with cutting teeth that protrude outwardly from one of two opposite broad sides of the blade, with the opposite broad side non-cutting. The cutting teeth may be oriented to cut when the blade moves in one direction and may be non-cutting when the blade moves opposite to the cutting direction.

BACKGROUND

A variety of surgical procedures can be performed to relieve pain in or restore function of various parts of a patient's body including conditions such as osteoarthritis, rheumatoid arthritis, or other joint conditions through minimally invasive or invasive surgery that involve bones. Such procedures may include resect one or more of the bones, including bones of one or more joints. For example, during partial or total knee replacement (TKR) arthroplasty, a surgeon may desire to resect bone to prepare the bone to accept an implant or prosthesis. A variety of resection instrumentation exists. However, in certain procedures a surgeon may desire to resect tissue (hard and/or soft) with a very fine degree of control and accuracy. Accordingly, a need exists for improved resection devices, systems, and/or methods that provide high degrees of accuracy, control, and precision. In this manner, a surgeon can resect as little of the tissue as needed for the procedure.

SUMMARY

The various apparatus, devices, systems, and/or methods of the present disclosure have been developed in response to the present state of the art, and in particular, in response to the problems and needs in the art that have not yet been fully solved by currently available resection instrumentation and/or processes.

To achieve the foregoing, and in accordance with the disclosure as embodied and broadly described herein, a surgical saw blade may be provided. One general aspect of the surgical saw blade can include a front side, an opposite back side, a top side, an opposite bottom side, a right side, and an opposite left side.

The surgical saw blade may also include a cutting tooth extending from the back side and having a cutting edge oriented toward one of the right side and the left side, the cutting tooth associated with an aperture through the saw blade between the front and back sides. The back side may be a single direction cutting side and the front, top, bottom, right, and left sides may be non-cutting sides. The surgical saw blade may also include a saw connection feature near the bottom side.

In one aspect, the aperture width for the aperture is 70% to 115% of a height for the cutting tooth. The surgical saw blade may also include one or more markings on the back side, the one or more markings configured to indicate that the back side is a cutting side. The one or more markings may include a direction marker that indicates which direction the single direction cutting side cuts in. In one aspect, the front side and the opposite back side are the broadest sides of the saw blade. In one aspect, the aperture is rectangular and comprises two parallel sides, an arcuate side that connects the two parallel sides and an open side in communication with the cutting edge of the tooth. In one aspect, the cutting edge can be one of arcuate or straight.

One general aspect can include an oscillating surgical saw blade that has a front side, an opposite back side, a top side, an opposite bottom side, a right side, and an opposite left side. The oscillating surgical saw blade may also have a plurality of cutting teeth connected to the back side and each cutting tooth may have a cutting edge oriented toward a common side of the oscillating saw blade. Each cutting tooth may be adjacent to an aperture through the saw blade between the front and back sides. The front, top, bottom, right, and left sides are non-cutting sides. The oscillating surgical saw blade can include an oscillating surgical saw connection feature near the bottom side that is connectable to an oscillating surgical driver of an oscillating surgical saw.

In one aspect an aperture width for the aperture of each of the plurality of cutting teeth is 70% to 115% of a height for the adjacent cutting tooth. In another aspect, the common side may include one of the right side and the left side. In one aspect, each cutting tooth includes a base, a cutting edge, a first side between the base and the cutting edge, the first side defining a first slot between the first side and the saw blade, a second side between the base and the cutting edge, the second side defining a second slot between the second side and the saw blade, where one end of the first slot includes a first scalloped edge and the opposite end of the first slot connects to the aperture, and where one end of the second slot includes a second scalloped edge and the opposite end of the second slot connects to the aperture.

In one aspect the first side may include a first side bevel and second side may include a second side bevel. The cutting edge may include a bevel may include opposite corner bevels and one or more front bevels. The plurality of cutting teeth are organized into a plurality of rows and columns. Each row of cutting teeth aligns with apertures of at least one adjacent row of cutting teeth.

One general aspect of the present disclosure can include an oscillating surgical saw blade that includes a front side, an opposite back side, a top side, an opposite bottom side, a right side, and an opposite left side; a set of cutting teeth organized into rows and columns; where the cutting teeth extend from the back side and each cutting tooth has a cutting edge oriented toward one of the right side and the left side, each cutting tooth associated with a rectangular aperture through the saw blade between the front and back sides; where an aperture width for each rectangular aperture is 70% to 115% of a height for each cutting tooth; and an oscillating saw connection feature near the bottom side, connectable to an oscillating surgical driver of an oscillating surgical saw.

Implementations may include one or more of the following features. The oscillating surgical saw blade where the cutting teeth in each column are aligned vertically and the cutting teeth in each row are aligned horizontally. Each row of cutting teeth aligns with apertures of at least one adjacent row of cutting teeth. Each cutting tooth may include: a base; the cutting edge; a first side between the base and the cutting edge, the first side defining a first slot between the first side and the saw blade; and a second side between the base and the cutting edge, the second side defining a second slot between the second side and the saw blade. First side and the second side are parallel to each other.

These and other features and advantages of the present disclosure will become more fully apparent from the following description and appended claims or may be learned by the practice of the disclosure as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

FIG. 5 is a top view of the surgical saw blade of FIG. 1, according to one embodiment;

FIG. 6 is a left view of the surgical saw blade of FIG. 1, according to one embodiment;

FIG. 7 is a front view of the surgical saw blade of FIG. 1, according to one embodiment;

FIG. 8 is a right view of the surgical saw blade of FIG. 1, according to one embodiment;

FIG. 9 is a back view of the surgical saw blade of FIG. 1, according to one embodiment;

FIG. 10 is a bottom view of the surgical saw blade of FIG. 1, according to one embodiment;

DETAILED DESCRIPTION

Figure 1:
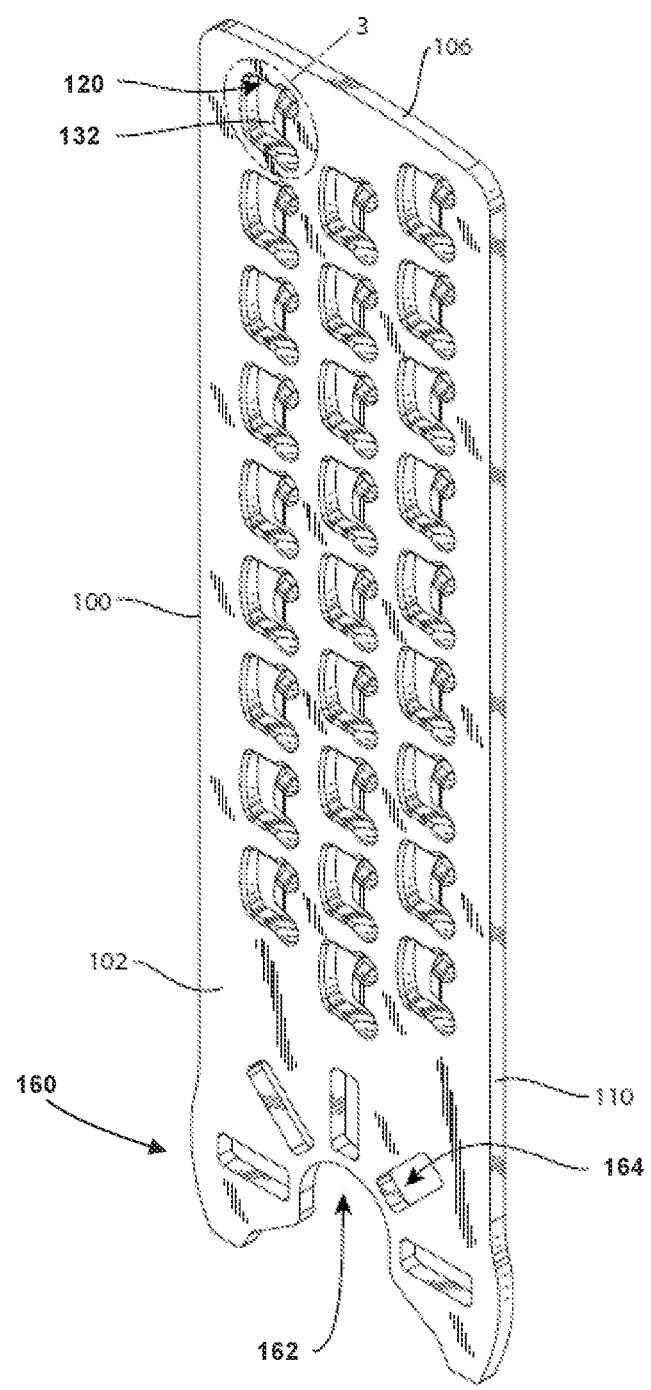
FIG. 1 is a perspective view of a surgical saw blade, according to one embodiment.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to or in communication with each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator. Dorsal means toward the top of the foot. Plantar means toward the sole of the foot.

Figure 2:
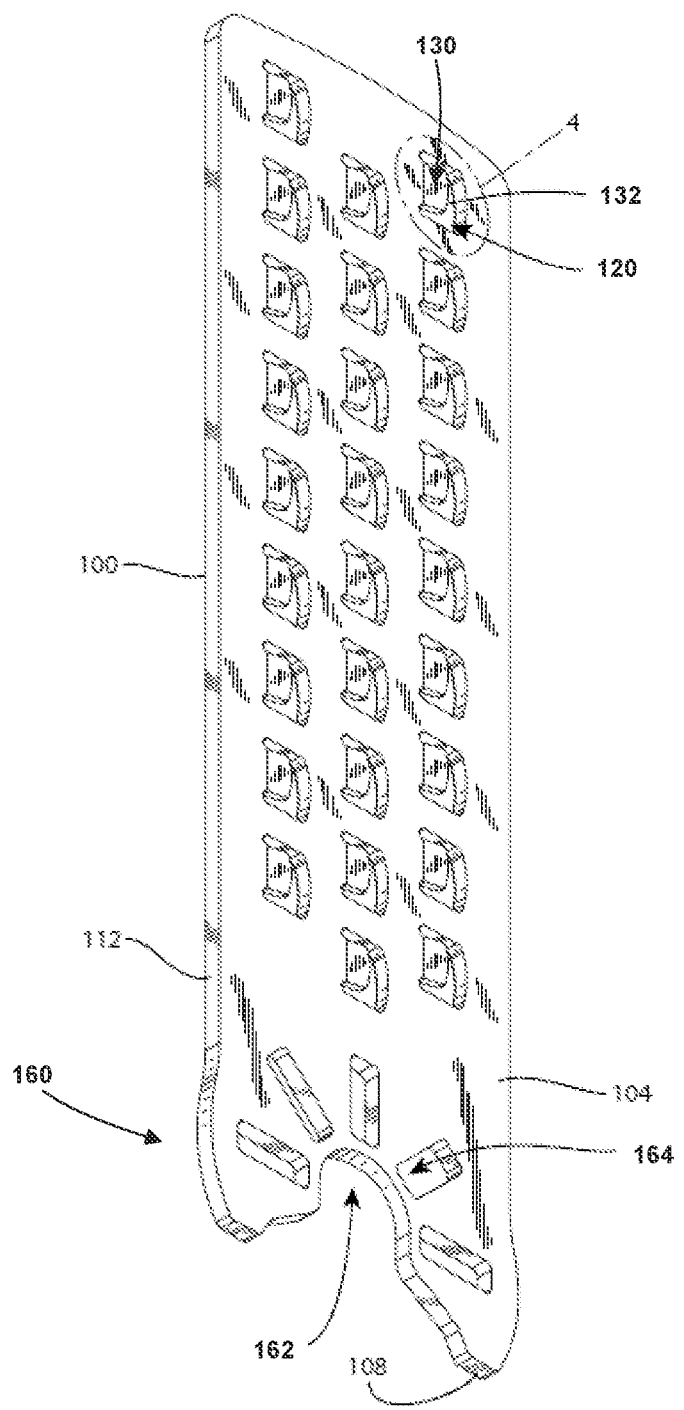
FIG. 2 is another perspective view of the surgical saw blade of FIG. 1 from a different direction, according to one embodiment.

Referring to FIGS. 1-2, a surgical saw blade 100 has a front side 102, an opposite back side 104, a top side 106, an opposite bottom side 108, a right side 110, and an opposite left side 112. The surgical saw blade 100 may have a variety of shapes and sizes. In one embodiment, the surgical saw blade 100 is rectangular having a right side 110 and left side 112 longer than a top side 106 and bottom side 108. In one embodiment, the right side 110 and left side 112 may be of similar length and the top side 106 and bottom side 108 may be of similar length.

The surgical saw blade 100 may include one or more apertures 120 which may extend through the surgical saw blade 100 between the front and back sides 102, 104. In one embodiment, each aperture 120 may have the same or a similar size and shape. Alternatively, or in addition, one or more apertures 120 may have the same or a similar size and shape and one or more other apertures 120 may have a different size and shape.

Each aperture 120 may include an associated cutting tooth 130. In one embodiment, each aperture 120 may be shaped to form a cutting tooth 130. In one embodiment, each aperture 120 may be sized relative to its cutting tooth 130 to be large enough to allow cutting debris to evacuate from the back side 104 through the aperture 120 toward the front side 102.

In one embodiment, the cutting tooth 130 may extend from the back side 104. In one embodiment, each cutting tooth 130 includes a cutting edge 132 oriented, or directed, toward one of the right side 110 and the left side 112. Having the cutting edge 132 of each cutting tooth 130 directed towards a single side, either a right side 110 or a left side 112 means that the cutting teeth 130 will cut in a single direction. If the cutting edge 132 of each cutting tooth 130 is directed towards the right side 110, the cutting teeth 130 will cut when the cutting teeth 130 are moved in the direction of the right side 110. If the cutting edge 132 of each cutting tooth 130 is directed towards the left side 112, the cutting teeth 130 will cut when the cutting teeth 130 are moved in the direction of the left side 112.

In the illustrated embodiment, the cutting teeth 130 extend from the back side 104 and from no other side of the surgical saw blade 100. Consequently, the back side 104 is a single direction cutting side. A single direction cutting side is a side of a structure that is configured to cut tissue, but generally cuts the tissue when the structure moves in a single direction and does not cut, or at least does not cut as effectively, in other directions. A single direction cutting side may also be referred to as a unidirectional cutting side, a one direction cutting side, or the like.

A surgical saw blade 100 with a single direction cutting side can help a surgeon to have more precise control of when and where and in which direction the surgical saw blade 100 will cut or resect tissue (e.g., hard or soft tissue). Having a back side 104 as a single direction cutting side can be advantageous because the back side 104 has a greater surface area than the top side 106, bottom side 108, right side 110, and/or left side 112. The greater surface area can facilitate larger planar cuts of tissue.

Because the cutting teeth 130 extend from the back side 104 and from no other side of the surgical saw blade 100. The front side 102, back side 104, top side 106, and bottom side 108 are non-cutting sides. A non-cutting side is a side of a structure that is configured to generally not cut tissue when placed in contact with the tissue, regardless of movement of the structure in any direction.

A surgical saw blade 100 with a single direction cutting side and the remaining sides non-cutting sides can help a surgeon by enabling the surgical saw blade 100 to be positioned in confined spaces around tissue that the surgeon does not want to cut and to contact targeted tissue with the single direction cutting side for very precise and targeted resection of tissue. Having a surgical saw blade 100 with a one of its six sides being a single direction cutting side and the five remaining sides being non-cutting sides enables the surgeon to position and maneuver the surgical saw blade 100 for very exact resection procedures on tissue.

The surgical saw blade 100 may include one or more features for connection to a powered handpiece (saw), handle, etc. In one embodiment, the surgical saw blade 100 may also include a saw connection feature 160 near the bottom side 108. Surgical saw blade 100 is shown with a group of saw connection features 160, including a notch 162 that extends into the surgical saw blade 100 through the bottom side 108 and a semi-circular array of rectangular apertures 164 arranged around the deepest portion of the notch 162. The illustrated group of saw connection features 160 is one example of a blade/saw interconnection.

Figure 3:
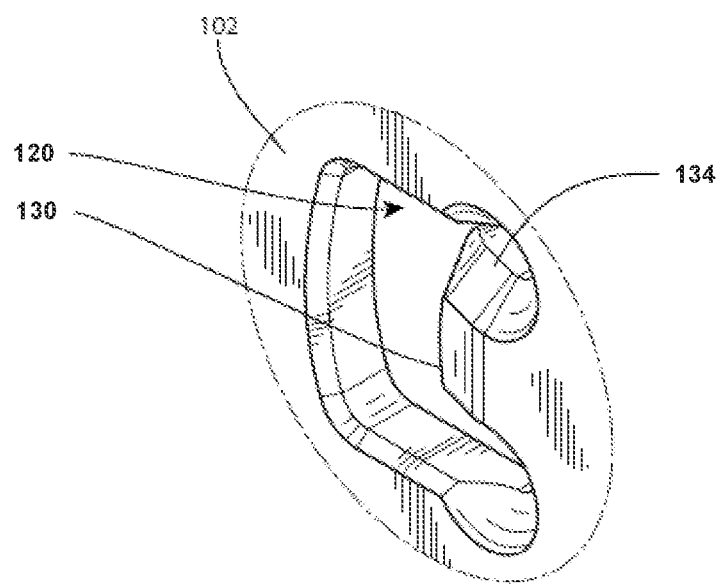
FIG. 3 is an enlarged detail view of a cutting tooth of the surgical saw blade of FIG. 1, as indicated by detail circle 3 of FIG. 1, according to one embodiment.
Figure 4:
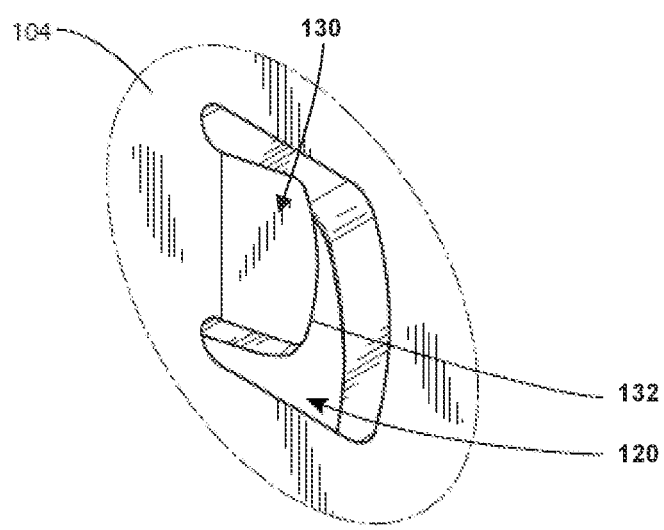
FIG. 4 is another enlarged detail view of the cutting tooth from a different direction, as indicated by detail circle 4 of FIG. 2, according to one embodiment.

FIGS. 3-4 illustrate enlarged detail of a cutting tooth of the surgical saw blade of FIG. 1, as indicated by detail circle 3 of FIG. 1 and enlarged detail view of the cutting tooth from a different direction, as indicated by detail circle 4 of FIG. 2, according to one embodiment. FIGS. 3-4 illustrate details of an aperture 120, cutting tooth 130, cutting edge 132, and a bevel 134.

FIGS. 5-10 illustrate a top view, front view, right view, back view, and bottom view respectively of the surgical saw blade of FIG. 1, according to one embodiment. In the illustrated embodiment, of FIGS. 5-10, the front side 102 and opposite back side 104 are the broadest sides of the surgical saw blade 100. While not drawn to scale, FIGS. 5-10 illustrate that the front side 102 and back side 104 are broader than the top side 106, bottom side 108, right side 110, and/or left side 112.

FIGS. 6-7 illustrate an embodiment in which the surgical saw blade 100 includes a plurality of cutting teeth 130 arranged, or organized, into a plurality of rows ($R_1$-$R_n$) and columns ($C_1$-$C_n$). In the illustrated embodiment, each row R of cutting teeth 130 is configured such that the plurality of cutting teeth 130 in each row R are aligned horizontally and each column C of cutting teeth 130 is configured such that the plurality of cutting teeth 130 in each column C are aligned vertically. Of course in other embodiments, cutting teeth 130 in one or more rows R may follow an arcuate path of alignment and/or cutting teeth 130 in one or more columns C may follow an arcuate path of alignment.

FIG. 7 illustrates one example of a variety of configurations of the apertures 120 and cutting teeth 130. In the illustrated embodiment, each row R of cutting teeth aligns with apertures 120 of at least one adjacent row R of cutting teeth 130. For example, row $R_1$ includes a single aperture 120a and single cutting tooth 130a. The cutting tooth 130a aligns horizontally with the two apertures 120 in the adjacent row $R_2$. Said another way, the apertures 120 and cutting teeth 130 of one row overlaps the apertures 120 and cutting teeth 130 of an adjacent row. In this manner, the cutting teeth 130 in row $R_1$ and row $R_2$ cooperate to engage the surface that the back side 104 contacts to make efficient cuts of the tissue. FIG. 7 includes the same overlap and/or alignment for cutting teeth 130 in the other rows $R_{1-n}$. FIG. 7 also illustrates that the apertures 120 of one row R overlap apertures 120 of an adjacent row R.

FIG. 7 illustrates an embodiment in which the that apertures 120 of one row R overlap apertures 120 of an adjacent row R and the cutting teeth 130 of one row R overlap apertures 120 of an adjacent row R. However, the cutting teeth 130 of one row R do not overlap cutting teeth 130 of an adjacent row R. This non-overlapping pattern of cutting teeth 130 may limit bone removal while the surgical saw blade 100 is actuated while being held in one location. Re-positioning the surgical saw blade 100 to a different location may permit additional bone removal. Alternatively, or in addition, in another embodiment, cutting teeth 130 of one row R may overlap cutting teeth 130 of an adjacent row R.

The surgical saw blade 100 may be designed for use with an oscillating saw that sweeps the surgical saw blade 100 side to side along an arcuate path 170 (See FIG. 7). When the surgical saw blade 100 is actuated in this way, the cutting teeth 130 cut bone, cartilage, or other hard or soft tissues next to, or against the back side 104 (i.e., a single direction cutting side) when the surgical saw blade 100 sweeps toward the left side 112. The cutting teeth 130 do not cut when the surgical saw blade 100 sweeps toward the right side 110, nor does the surgical saw blade 100 cut tissues that are next to, or against the front, right, and/or left side 102, 110, 112 (i.e., non-cutting sides).

Referring to FIG. 7, the cutting tooth 130 inside the detail circle 11 is offset toward the top (free end, top side 106) of the surgical saw blade 100 relative to the top cutting tooth 130b in the center column. In one embodiment, the offset may be equal to the width of the tooth 130. Each cutting tooth 130 may be angled or bent so that the free end (i.e., cutting edge 132) of the cutting tooth 130 protrudes outwardly from the remainder of the surgical saw blade 100. The cutting teeth 130 are shown protruding outwardly from the back side 104. Each cutting tooth 130 may include one or more side bevels 134 (See FIG. 11) along the edge(s) of the tooth, which may sharpen the tooth for cutting along the back side 104.

FIG. 8 illustrates a right side 110 view. FIG. 9 illustrates a back side 104 view. FIG. 10 illustrates a bottom side 108 view. In FIGS. 7 and 9, surgical saw blade 100 is shown with twenty-seven apertures 120 and cutting teeth 130 arranged in three columns of nine apertures/teeth. The rows may be staggered as shown so that the cutting teeth 130 in adjacent rows are offset for maximum cutting coverage. In one embodiment, certain parts of rows or columns may include no apertures 120, no cutting teeth 130, or neither apertures 120 nor cutting teeth 130.

Figure 11:
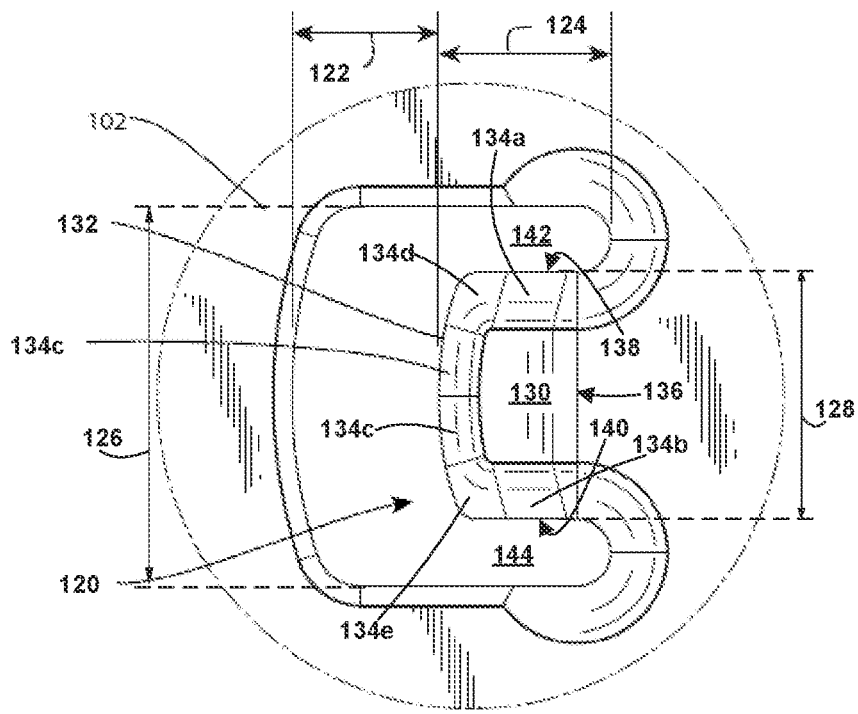
FIG. 11 is an enlarged detail view of the cutting tooth, as indicated by detail circle 11 of FIG. 7, according to one embodiment.
Figure 12:
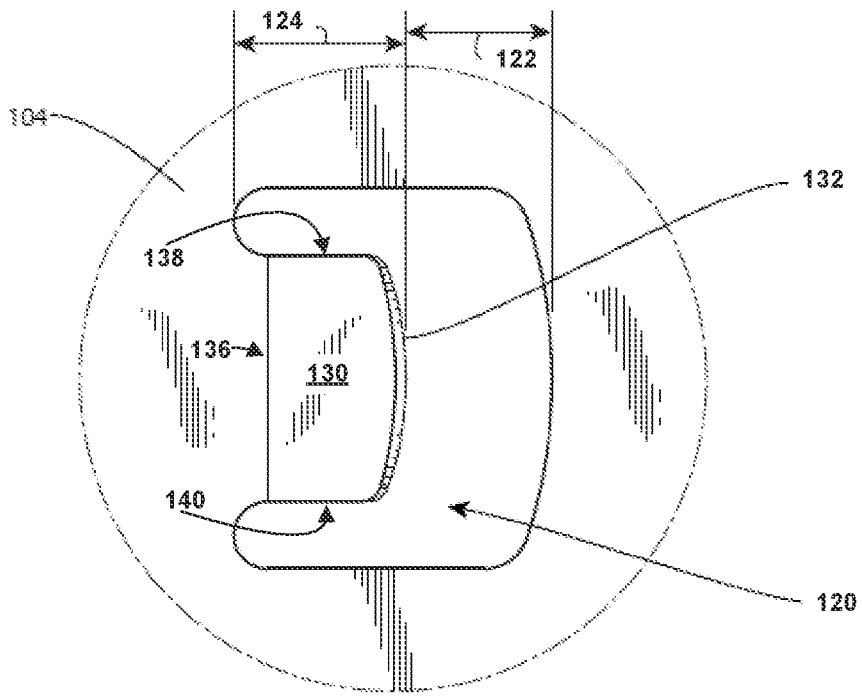
FIG. 12 is an enlarged detail view of the cutting tooth, as indicated by detail circle 12 of FIG. 9, according to one embodiment.

FIG. 11 is an enlarged detail view of the cutting tooth, as indicated by detail circle 11 of FIG. 7, according to one embodiment and FIG. 12 is an enlarged detail view of the cutting tooth, as indicated by detail circle 12 of FIG. 9, according to one embodiment.

Referring to FIGS. 11-12, the aperture width 122 may be a percentage of the cutting tooth height 124. The percentage of the aperture width 122 in relation to the cutting tooth height 124 may be 70% to 115%. In some embodiments, the percentage may be 75%±5%, 80%±5%, 85%±5%, 90%±5%, 95%±5%, 100%±5%, 105%±5%, 110%±5%, or any other range within 70% to 115%. The aperture height 126 may be greater than a cutting tooth width 128. In one embodiment, the aperture 120 has a rectangular shape. In the illustrated embodiment, the aperture 120 has two parallel sides that are connected by an arcuate side. The aperture 120 includes an open side that is in communication with the cutting edge 132. Alternatively, or in addition, the aperture 120 may include be straight instead of arcuate as depicted in FIG. 11. In certain embodiments, the aperture 120 is considered adjacent to the cutting tooth 130.

In one embodiment, the cutting tooth 130 includes a base 136, the cutting edge 132, a first side 138, and a second side 140. The base 136 connects the cutting tooth 130 to the surgical saw blade 100. The first side 138 extends between the base 136 and the cutting edge 132. The first side 138 defines a first slot 142 between the first side 138 and the surgical saw blade 100. The first side 138 includes a first side bevel 134a that extends between the first side 138 and a surface of the cutting tooth 130.

The second side 140 extends between the base 136 and the cutting edge 132 on a side opposite the first side 138. The second side 140 defines a second slot 144 between the second side 140 and the surgical saw blade 100. The second side 140 includes a second side bevel 134b that extends between the second side 140 and a surface of the cutting tooth 130. In certain embodiments, the first side bevel 134a and second side bevel 134b slope at the same angle and are the same size/shape. In another embodiment, the first side bevel 134a and second side bevel 134b slope at different angles and have different sizes/shapes. In one embodiment, the first side bevel 134a and second side bevel 134b are parallel to each other. In another embodiment, the first side bevel 134a and second side bevel 134b may be angled in relation to each other such that the side bevels 134 are closer to each other near the cutting edge 132.

The cutting edge 132 can have a variety of shapes and sizes based on the kind of tissue the surgical saw blade 100 is designed to cut. In the illustrated embodiment, the cutting edge 132 is arcuate and extends from the first side 138 to the second side 140. The cutting edge 132 can have a convex shape or a concave shape.

In one embodiment, the cutting edge 132 includes a bevel 134. The bevel 134 can be made up of one or more other bevels. For example, the bevel 134 can include one or more front bevels 134c and corner bevels d,e on opposite ends of the bevel 134. In the illustrated embodiment, the cutting tooth 130 includes two front bevels 134. Of course, the cutting edge 132 may include two or more front bevels 134.

The bevels 134 cooperate to provide a sharped edge for the cutting edge 132 to facilitate cutting of the tissue. Those of skill in the art will recognize that the bevels 134a-e may have uniform angles, shapes, and sizes. Alternatively, or in addition, the bevels 134a-e may each have a variety of different combinations of angles, shapes, and sizes.

The first slot 142 includes a first scalloped edge 146 at one end and an opposite end that connects to and is in communication with the aperture 120. The second slot 144 includes a second scalloped edge 148 at one end and an opposite end that connects to and is in communication with the aperture 120. In one embodiment, the first scalloped edge 146 and second scalloped edge 148 are concave structures at the end of the first slot 142 and second slot 144 respectively. The first scalloped edge 146 and second scalloped edge 148 can facilitate evacuation of debris while the surgical saw blade 100 is cutting. In particular, the first scalloped edge 146 and second scalloped edge 148 can facilitate evacuation of debris from the back side 204 through the aperture toward the front side 202.

In one embodiment, the first slot 142 and second slot 144 are of similar shape and size. The first slot 142 and second slot 144 may be sized and shaped to facilitate evacuation of debris from the back side 204 through the aperture 120 toward the front side 202.

Figure 13:
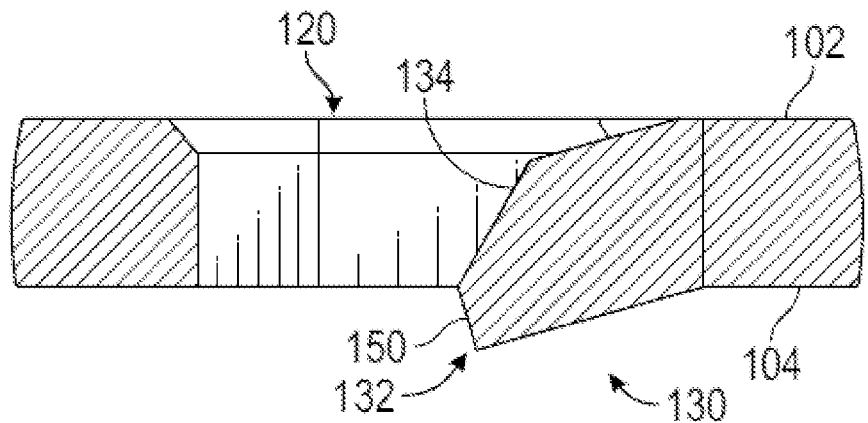
FIG. 13 is a cross-sectional view of the cutting tooth, taken along section line 13-13 of FIG. 7, according to one embodiment.

FIG. 13 illustrates a cross-sectional view of the cutting tooth 130, taken along section line 13-13 of FIG. 7, according to one embodiment. In the illustrated embodiment, the cutting edge 132 includes a face 150. In this embodiment, the face 150 is flat and connects to a bottom surface of the cutting tooth 130 at a right angle and to the bevel 134 at an angle greater than 90 degrees.

Figure 14:
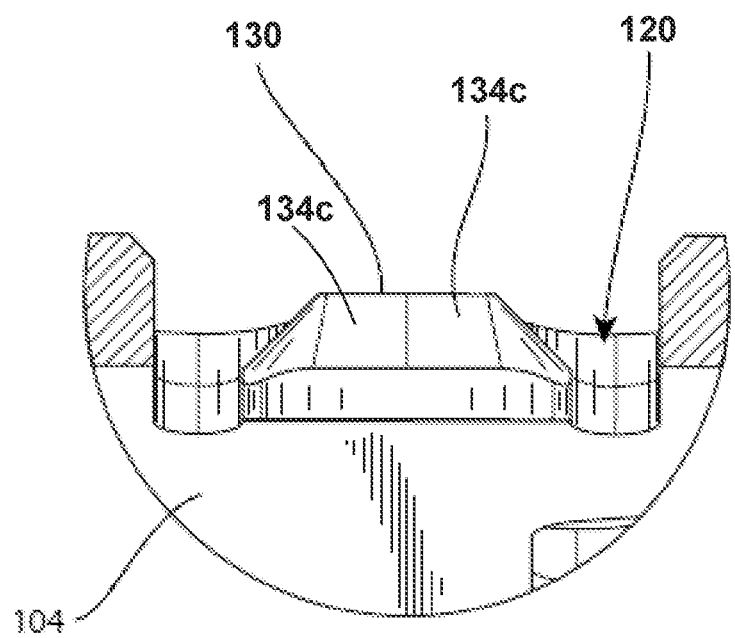
FIG. 14 is a cross-sectional view of the cutting tooth, taken along section line 14-14 of FIG. 10, according to one embodiment.

FIG. 14 illustrates a cross-sectional view of the cutting tooth 130, taken along section line 14-14 of FIG. 10, according to one embodiment. FIG. 14 illustrates details of one embodiment of the aperture 120, cutting tooth 130, and one or more front bevels 134c.

Referring to FIGS. 15-28, another embodiment of an oscillating surgical saw blade 200 has a front side 202, an opposite back side 204, a top side 206, an opposite bottom side 208, a right side 210, and an opposite left side 212.

The oscillating surgical saw blade 200 may include one or more apertures 220 which may extend through the saw blade 200 between the front and back sides 202, 204. The oscillating surgical saw blade 200 can include a plurality of cutting teeth 230.

In one embodiment, each aperture can be shaped to form a cutting tooth 230. Alternatively, each aperture 220 is adjacent to a cutting tooth 230. Each aperture 220 may be sized relative to its cutting tooth 230 to be large enough to allow cutting debris to evacuate from the back side 204 through the aperture toward the front side 202.

In one embodiment, a plurality of cutting teeth 230 may be connected to the back side 204. In one embodiment, each cutting tooth 230 includes a cutting edge 232 oriented, or directed, toward a common side. In one embodiment, the common side is the right side 210. In another embodiment, the common side is the left side 212. Having the cutting edge 232 of each cutting tooth 230 directed towards a single side, the common side means that the cutting teeth 230 will cut in a single direction. If the cutting edge 232 of each cutting tooth 230 is directed towards the right side 210, the cutting teeth 230 will cut when the cutting teeth 230 are moved in the direction of the right side 210. If the cutting edge 232 of each cutting tooth 230 is directed towards the left side 212, the cutting teeth 230 will cut when the cutting teeth 230 are moved in the direction of the left side 212.

In the illustrated embodiment, the cutting teeth 230 extend from the back side 204 and from no other side of the oscillating surgical saw blade 200. Consequently, the back side 204 is a single direction cutting side. A single direction cutting side is a side of a structure that is configured to cut tissue, but generally cuts the tissue when the structure moves in a single direction and does not cut, or at least does not cut as effectively, in other directions.

An oscillating surgical saw blade 200 with a single direction cutting side can provide a surgeon more precise control of when, and where, and in which direction, the oscillating surgical saw blade 200 will cut or resect tissue (e.g., hard or soft tissue). Having a back side 204 as a single direction cutting side can be advantageous because the back side 204 has a greater surface area than the top side 206, bottom side 208, right side 210, and/or left side 212. The greater surface area can facilitate larger planar cuts of tissue.

Because the cutting teeth 230 extend from the back side 204 and from no other side of the oscillating surgical saw blade 200. The front side 202, back side 204, top side 206, and bottom side 208 are non-cutting sides. An oscillating surgical saw blade 200 with a single direction cutting side (e.g., back side 204) and the remaining sides non-cutting sides can help a surgeon by enabling the oscillating surgical saw blade 200 to be positionable in confined spaces around tissue that the surgeon does not want to cut and to contact targeted tissue with the single direction cutting side for very precise and targeted resection of tissue. Having an oscillating surgical saw blade 200 with a one of its six sides being a single direction cutting side and the five remaining sides being non-cutting sides enables the surgeon to position and maneuver the oscillating surgical saw blade 200 for very exact resection procedures on tissue.

Figure 15:
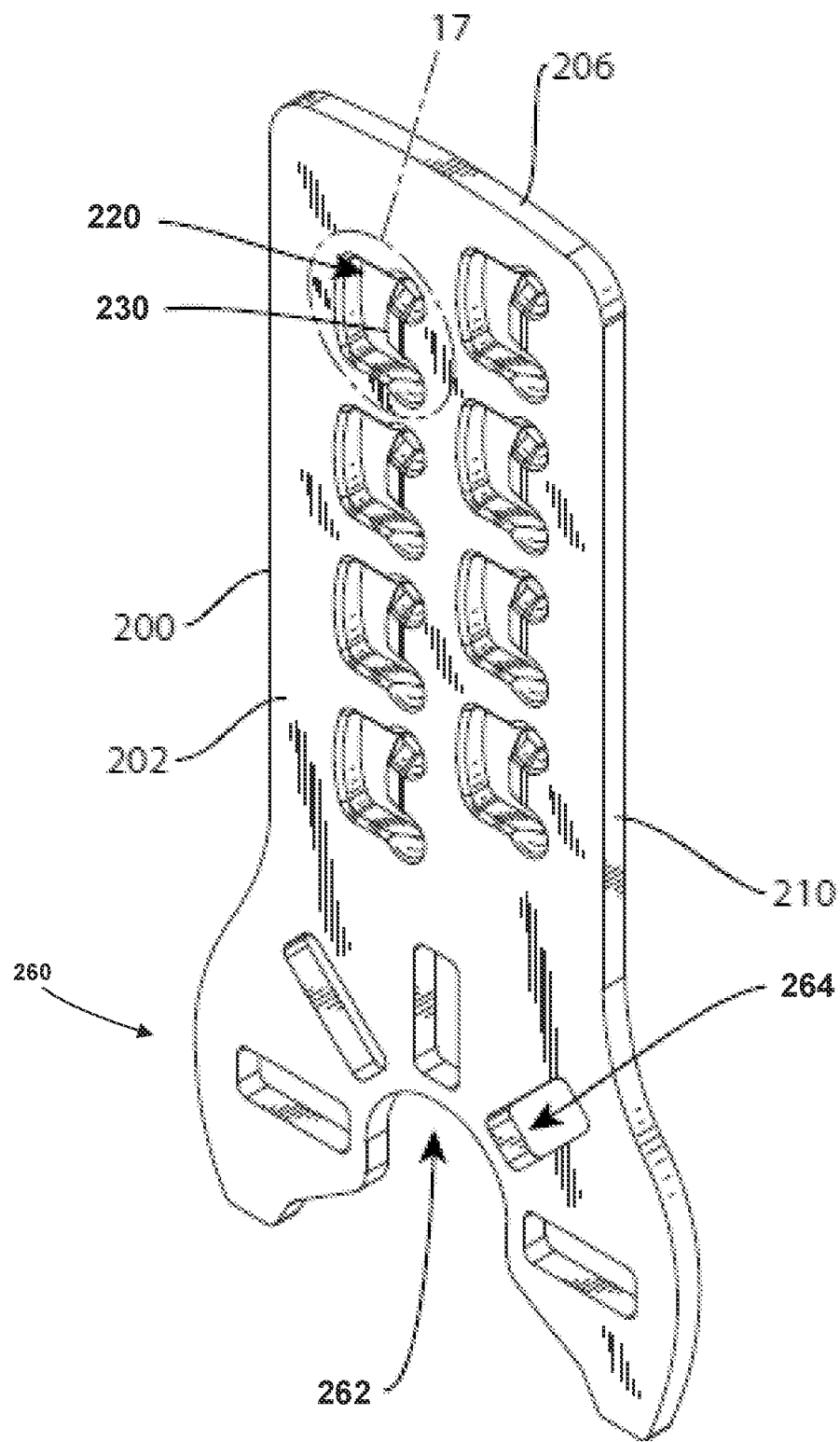
FIG. 15 is a perspective view of another surgical saw blade, according to one embodiment.
Figure 16:
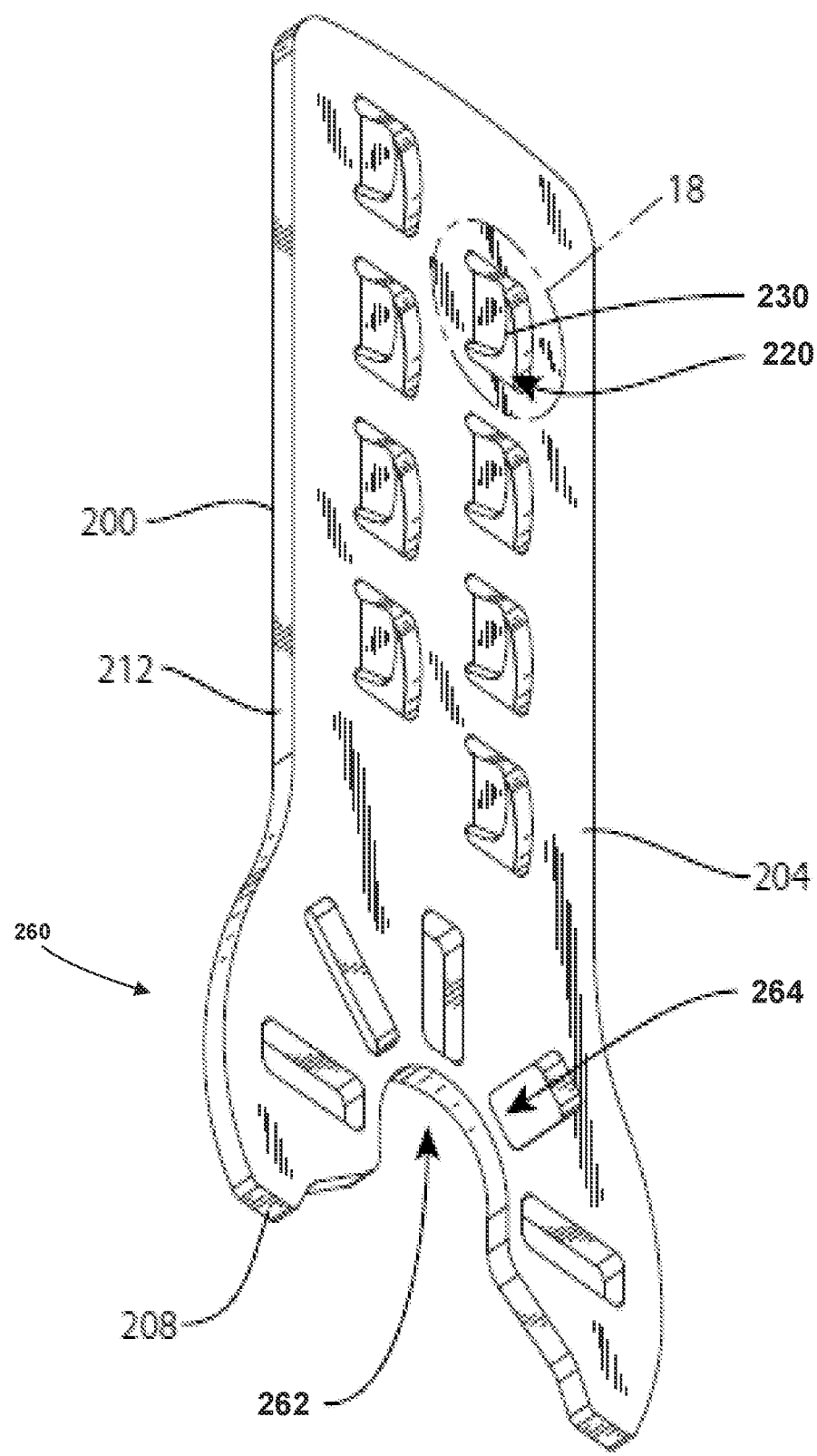
FIG. 16 is another perspective view of the surgical saw blade of FIG. 15 from a different direction, according to one embodiment.

Referring to FIGS. 15-16, the saw blade 200 may include one or more features for connection to a powered handpiece (saw), handle, etc. Oscillating surgical saw blade 200 is shown with a group of saw connection features 260, including a notch 262 that extends into the saw blade 200 through the bottom side 208 and a semi-circular array of rectangular apertures 264 arranged around the deepest portion of the notch 262. The illustrated group of saw connection features 262, 264 is one example of a blade/saw interconnection. Notch 262 may be identical to notch 162, apertures 264 may be identical to apertures 164, and the blade/saw interconnections shown for saw blades 100, 200 may be identical so that saw blades 100, 200 may be used interchangeably with a powered saw handpiece, etc.

Figure 17:
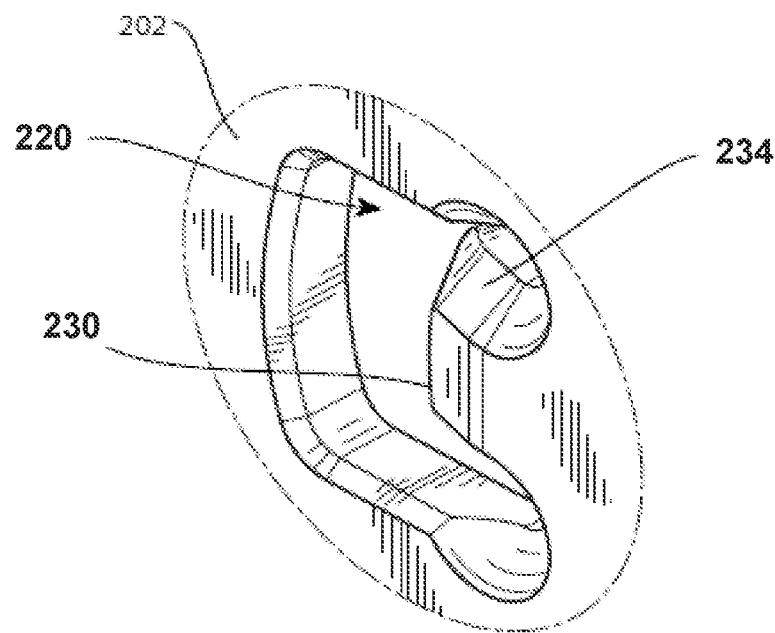
FIG. 17 is an enlarged detail view of a cutting tooth of the surgical saw blade of FIG. 15, as indicated by detail circle 17 of FIG. 15, according to one embodiment.
Figure 18:
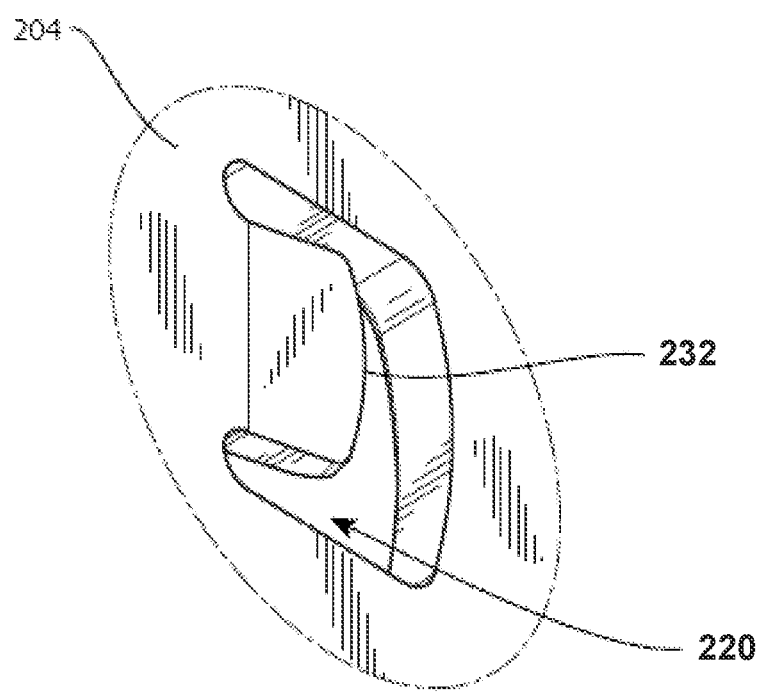
FIG. 18 is another enlarged detail view of the cutting tooth from a different direction, as indicated by detail circle 18 of FIG. 16, according to one embodiment.
Figure 19:
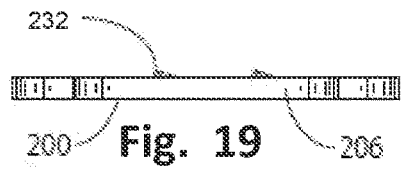
FIG. 19 is a top view of the surgical saw blade of FIG. 15, according to one embodiment.

FIGS. 17-18 illustrate enlarged detail of a cutting tooth of the oscillating surgical saw blade 200 of FIG. 15, as indicated by detail circle 17 of FIG. 15 and enlarged detail view of the cutting tooth from a different direction, as indicated by detail circle 18 of FIG. 16, according to one embodiment. FIGS. 17-18 illustrate details of an aperture 220, cutting tooth 230, cutting edge 232, and a bevel 234.

FIGS. 19-24 illustrate a top view, front view, right view, back view, and bottom view respectively of the oscillating surgical saw blade 200 of FIG. 15, according to one embodiment. In the illustrated embodiment, of FIGS. 19-24, the front side 202 and opposite back side 204 are the broadest sides of the oscillating surgical saw blade 200. While not necessarily drawn to scale, FIGS. 19-24 illustrate that the front side 202 and back side 204 are broader than the top side 206, bottom side 208, right side 210, and/or left side 212.

Referring now to FIGS. 7, 9, 21, and 23, the oscillating surgical saw blade 200 may include apertures 220 and/or cutting teeth 230 organized into rows and columns. The oscillating surgical saw blade 200 has fewer columns and rows than the surgical saw blade 100 embodiment illustrated in FIGS. 7 and 9. Furthermore, the apertures 220 of the oscillating surgical saw blade 200 can be described as rectangular apertures because of their generally rectangular shape. In one embodiment, each rectangular aperture 220 may be 70% to 115% of a height of an associated cutting tooth 230.

Figure 25:
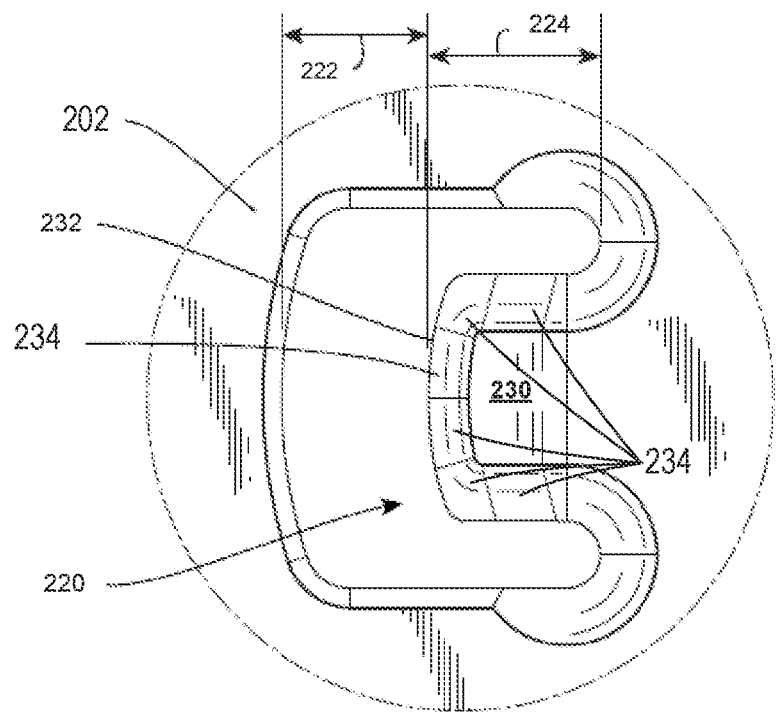
FIG. 25 is an enlarged detail view of the cutting tooth, as indicated by detail circle 25 of FIG. 21, according to one embodiment.
Figure 26:
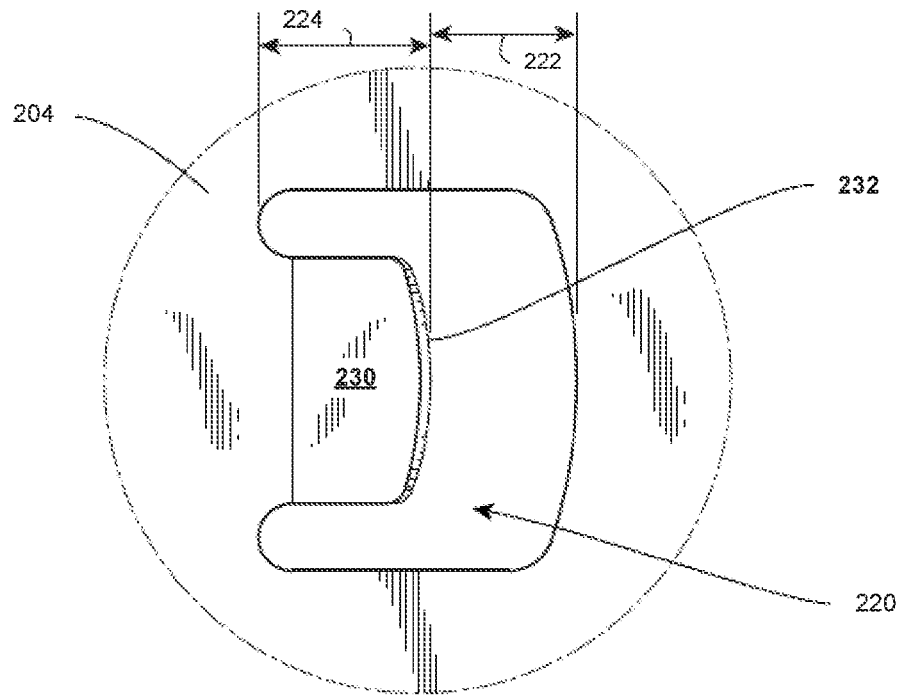
FIG. 26 is an enlarged detail view of the cutting tooth, as indicated by detail circle 26 of FIG. 23, according to one embodiment.

Referring to FIGS. 25-26, the aperture width 222 may be a percentage of the cutting tooth height 224 of an adjacent cutting tooth 230. The percentage may be 70% to 115%. In some embodiments, the percentage may be 75%±5%, 80%±5%, 85%±5%, 90%±5%, 95%±5%, 100%±5%, 105%±5%, 110%±5%, or any other range within 70% to 115%. Saw blade 200 is shown with eight apertures 220 and cutting teeth 230 arranged in two columns of four apertures/teeth. The rows may be staggered as shown so that the cutting teeth 230 in adjacent rows are offset for maximum cutting coverage.

Figures 20, 21:
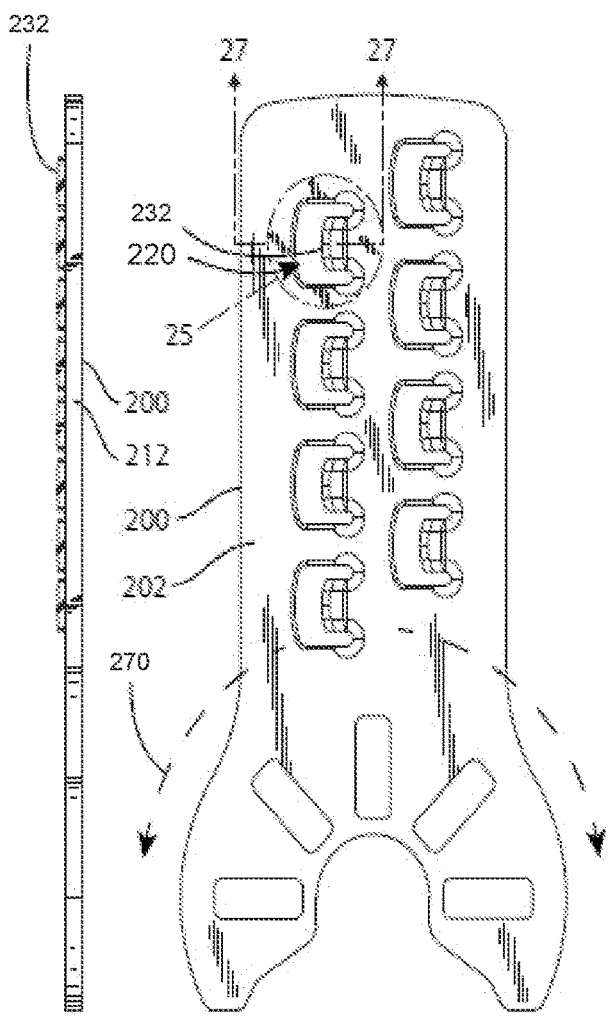
FIG. 20 is a left view of the surgical saw blade of FIG. 15, according to one embodiment.
FIG. 21 is a front view of the surgical saw blade of FIG. 15, according to one embodiment.
Figures 22, 23:
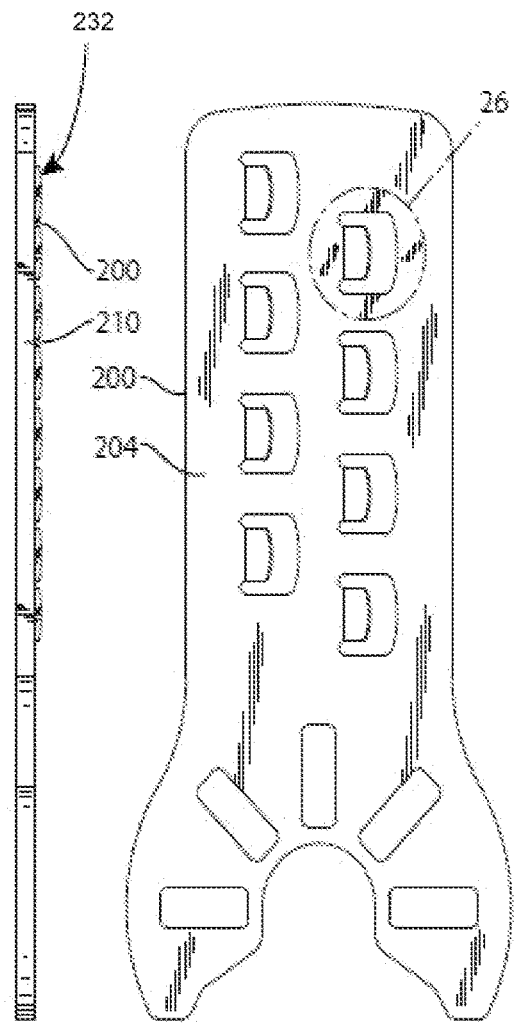
FIG. 22 is a right view of the surgical saw blade of FIG. 15, according to one embodiment.
FIG. 23 is a back view of the surgical saw blade of FIG. 15, according to one embodiment.

Referring to FIGS. 21 and 25, the cutting tooth 230 inside the detail circle 25 is offset away from the top (free end) of the oscillating surgical saw blade 200 relative to the top cutting tooth in the other row; the offset may be equal to the width of the tooth. Each cutting tooth 230 may be angled or bent so that the free end (the cutting edge 232) of the cutting tooth 230 protrudes outwardly from the remainder of the saw blade 200. The cutting teeth 230 are shown protruding outwardly from the back side 204. Each cutting tooth 230 may include one or more bevels 234 along the front side of the tooth, which may sharpen the tooth for cutting along the back side.

The oscillating surgical saw blade 200 is designed for use with an oscillating saw that sweeps the saw blade 200 side to side along an arcuate path 270 (FIG. 21). When the saw blade 200 is actuated in this way, the cutting teeth 230 cut bone, cartilage, or other hard or soft tissues next to or against the back side 204 when the saw blade 200 sweeps toward the left side 212. The cutting teeth 230 do not cut when the oscillating surgical saw blade 200 sweeps toward the right side 210, nor does the saw blade 200 cut tissues that are next to, or against the front, right, and/or left side 202, 210, 212. The non-overlapping pattern of cutting teeth 230 may limit bone removal while the saw blade 200 is actuated while being held in one location; moving the saw blade 200 to a different location may permit additional bone removal. The back side 204 may be referred to as a cutting side of the saw blade 200, and the front, right, and/or left side 202, 210, 212 may be referred to as a non-cutting side.

While the saw blades 100, 200 are shown with rectilinear arrays of cutting teeth 130, 230, in other examples the teeth may be positioned in any array configuration. Some examples include arcuate, spiral, or other polynomial. In one example, the teeth may be arranged along arcuate paths that are all concentric with the center point of saw blade oscillation, optionally including the tooth offset discussed above.

Figure 27:
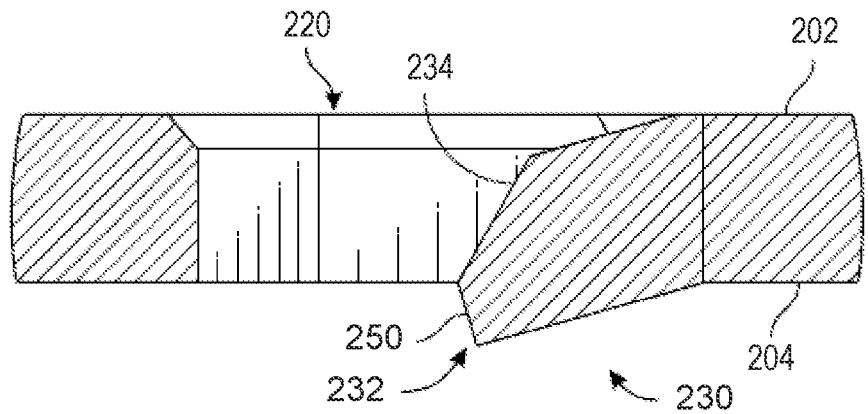
FIG. 27 is a cross-sectional view of the cutting tooth, taken along section line 27-27 of FIG. 21, according to one embodiment.

FIG. 27 illustrates a cross-sectional view of the cutting tooth 230, taken along section line 27-27 of FIG. 21, according to one embodiment. In the illustrated embodiment, the cutting edge 232 includes a face 250. In this embodiment, the face 250 is flat and connects to a bottom surface of the cutting tooth 230 at a right angle and to the bevel 234 at an angle greater than 90 degrees.

Figure 24:
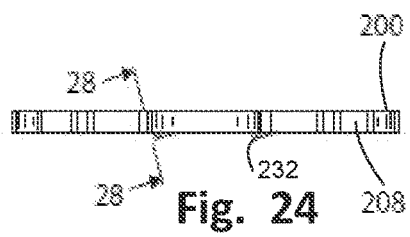
FIG. 24 is a bottom view of the surgical saw blade of FIG. 15, according to one embodiment.
Figure 28:
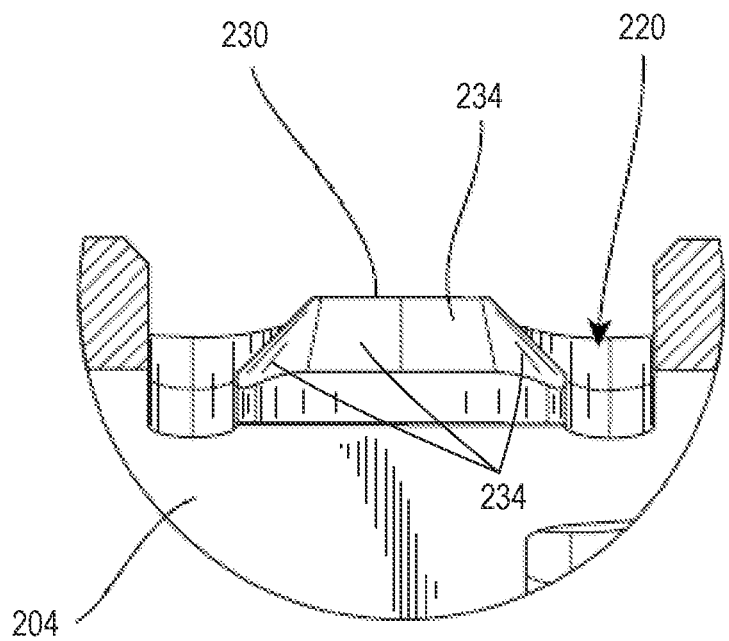
FIG. 28 is a cross-sectional view of the cutting tooth, taken along section line 28-28 of FIG. 24, according to one embodiment.

FIG. 28 illustrates a cross-sectional view of the cutting tooth 230, taken along section line 28-28 of FIG. 24, according to one embodiment. FIG. 28 illustrates details of one embodiment of the aperture 220, cutting tooth 230, and one or more front bevels 234.

Figure 29:
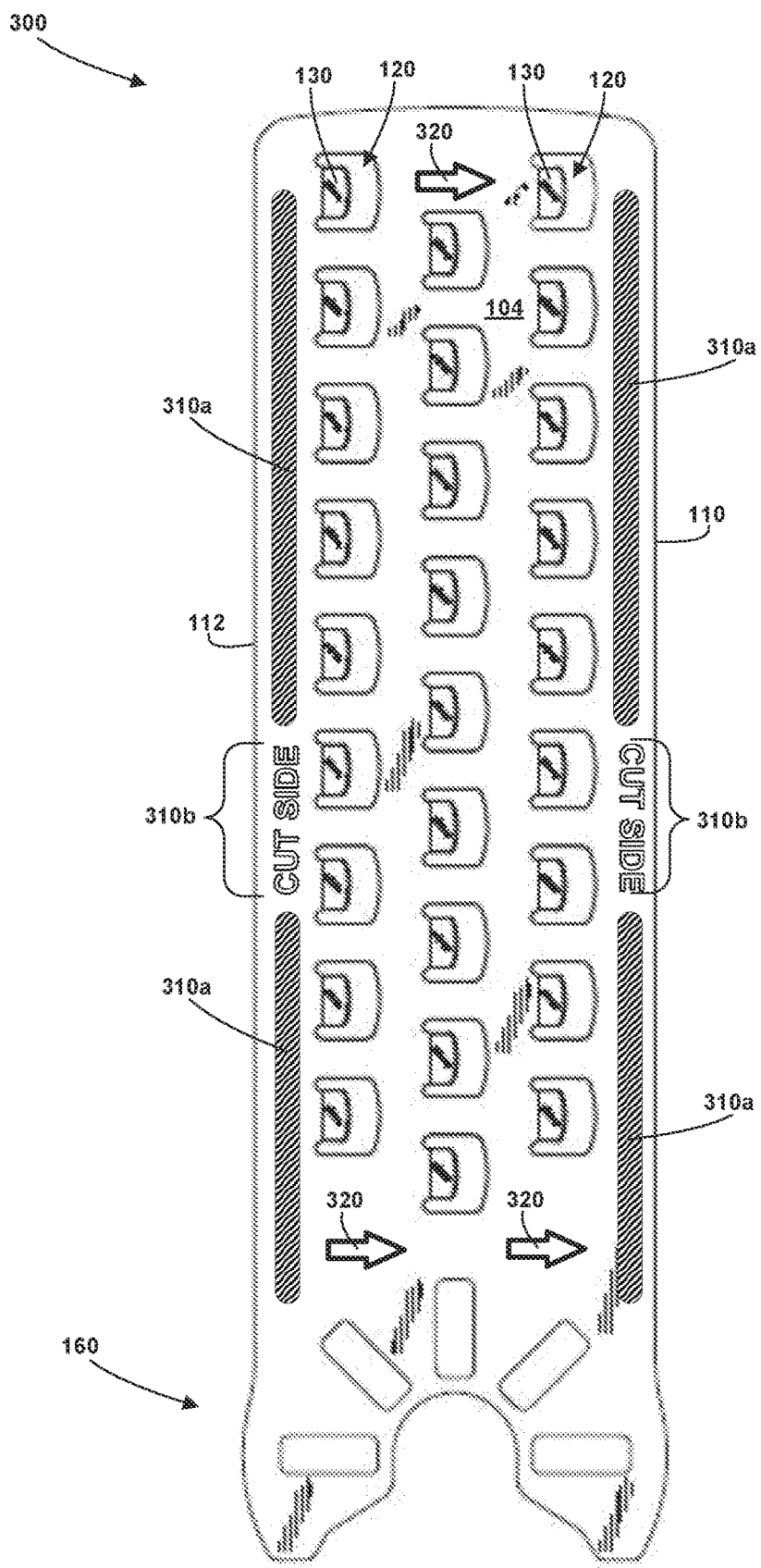
FIG. 29 is a back view of a surgical saw blade, according to one embodiment.

FIG. 29 is a back view of a surgical saw blade 300, according to one embodiment. The surgical saw blade 300 may have structures, features, functions, operations, and a configuration similar to that of the surgical saw blade 100 or oscillating surgical saw blade 200 described above. Where these structures are substantially the same, like numerals are used to identify the corresponding parts. In the illustrated embodiment, the surgical saw blade 300 includes one or more features that other embodiments may not include.

In particular, the surgical saw blade 300 may include one or more markings 310 and/or one or more direction markers 320. Marking 310 may be a symbol, shape, logo, set of letters or words, or any other indicia to indicate to a user that the side that includes the marking 310 is a cutting side or a single direction cutting side. The one or more markings 310 and/or one or more direction markers 320 may serve to quickly indicate to a user which side is the cutting side. This can help the user in determining how to orient the surgical saw blade 300 and/or how to install the surgical saw blade 300 on a powered handpiece (saw), handle, etc.

FIG. 29 illustrates two different types of one or more markings 310 that may be used in various embodiments. As illustrated, in one embodiment, marking 310a is a slot shape with a cross-hatching fill. Alternatively, or in addition, a marking 310b may be used. The marking 310b may include text in a language of the intended user that states that the side with the marking 310b is the cutting side. In the illustrated embodiment, the one or more markings 310 are applied to the back side 104 because the back side 104 is the cutting side. More specifically, in this embodiment, the back side 104 is a single direction cutting side. The one or more markings 310 may be printed on the surgical saw blade 300 or etched on using laser techniques.

In one embodiment, the direction marker 320 can be applied to one side (e.g., a back side 104) to indicate to a user which direction a single direction cutting side cuts in. Alternatively, or in addition, one or more direction markers 320 can be applied to another side (e.g., a front side 102 not shown) to indicate to a user which direction a single direction cutting side cuts in.

In the illustrated embodiment, the direction marker 320 is an arrow positioned so that the point of the arrow points toward right side 110 because this is the direction the cutting teeth 130 are oriented to cut in. The direction marker 320 may or may not include a fill. The direction marker 320 may be printed on the surgical saw blade 300 or etched on using laser techniques.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

As used herein, "side" refers to structure or part of a structure including, but not limited to: one of a longer bounding surfaces or lines of an object especially contrasted with the ends, a line or surface forming a border or face of an object, either surface of a thin object, a bounding line or structure of a geometric figure or shape. (search "side" on Merriam-Webster.com. Merriam-Webster, 2021. Web. 3 Aug. 2021. Modified.) A side can also refer to a geometric edge of a polygon (two-dimensional shape) and/or a face or surface of a polyhedron (three-dimensional shape). (Search "side" on Wikipedia.com Jul. 21, 2021. CC-BY-SA 3.0 Modified. Accessed Aug. 3, 2021.)

As used herein, "edge" refers to a structure or line where an object or area begins or ends. an edge can also refer to a narrow part adjacent to a border (search "edge" on Merriam-Webster.com. Merriam-Webster, 2021. Web. 3 Aug. 2021. Modified.)

As used herein, "cutting edge" refers to an edge designed, adapted, configured, or engineered to facilitate cutting into another structure or object to remove parts of the structure or object and/or to cut through the structure or object. Examples of a cutting edge, include, but are not limited to, an edge of a knife, tooth, blade, saw, or the like.

As used herein, "feature" refers to a distinctive attribute or aspect of something. (Search "feature" on google.com. Oxford Languages, 2021. Web. 20 Apr. 2021.) A feature may include one or more modifiers that identify one or more particular functions, attributes, advantages, or operations and/or particular structures relating to the feature. Examples of such modifiers applied to a feature, include, but are not limited to, "attachment feature," "securing feature," "alignment feature," "adjustment feature," "guide feature," "protruding feature," "engagement feature," "fixation feature", "disengagement feature," and the like.

As used herein, a "base" refers to a main or central structure, component, or part of a structure. A base is often a structure, component, or part upon which, or from which other structures extend, are coupled to, or connect to. A base may have a variety of geometric shapes and configurations. A base may be rigid or pliable. A base may be solid or hollow. In one embodiment, a base may include a housing, frame, or framework for a larger system, component, structure, or device. In certain embodiments, a base can be a part at the bottom or underneath a structure designed to extend vertically when the structure is in a desired configuration or position.

As used herein, "slot" refers to a narrow opening or groove. (search "direction" on Merriam-Webster.com. Merriam-Webster, 2021. Web. 4 Aug. 2021. Modified.)

As used herein, "bevel" refers to an edge of a structure that is not perpendicular to the faces of the piece, the edge has a slope or slant or angled profile and can refer to a sloped surface. Often a cutting tool such as a blade or tooth can have a beveled edge that facilitates the cutting edge in cutting into a target material. "bevel" and "chamfer" can be used interchangeably herein. (Search "bevel" on Wikipedia-.com May 17, 2021. CC-BY-SA 3.0 Modified. Accessed Aug. 4, 2021; search "bevel" on Merriam-Webster.com. Merriam-Webster, 2021. Web. Accessed 4 Aug. 2021. Modified; search "bevel" on wordhippo.com. WordHippo, 2021. Web. Accessed 4 Aug. 2021. Modified.)

As used herein, "row" refers to a number of objects arranged or aligned such that they follow an organized line. Typically, the organized line is a straight horizontal line. In certain embodiments, the organized line can be a curved line or may extend in a vertical and horizontal direction. (search "row" on Merriam-Webster.com. Merriam-Webster, 2021. Web. Accessed 4 Aug. 2021. Modified).

As used herein, "column" refers to a number of objects arranged or aligned such that they follow an organized generally vertical line. Typically, the organized line is a straight vertical line. In certain embodiments, the organized line can be a curved line that extends vertically. (search "column" on Merriam-Webster.com. Merriam-Webster, 2021. Web. Accessed 4 Aug. 2021. Modified).

As used herein, an "aperture" refers to a gap, a hole, a port, a portal, an opening, a space or recess in a structure, a void in a structure, or the like. In certain embodiments, an aperture can refer to a structure configured specifically for receiving something and/or for allowing access. In certain embodiments, an aperture can pass through a structure. In other embodiments, an aperture can exist within a structure but not pass through the structure. An aperture can be two-dimensional or three-dimensional and can have a variety of geometric shapes and/or cross-sectional shapes, including, but not limited to a rectangle, a square, or other polygon, as well as a circle, an ellipse, an ovoid, or other circular or semi-circular shape.

As used herein, "end" refers to a part or structure of an area or span that lies at the boundary or edge. An end can also refer to a point that marks the extent of something and/or a point where something ceases to exist. An end can also refer to an extreme or last part lengthwise of a structure or surface. (search "end" on Merriam-Webster.com. Merriam-Webster, 2021. Web. 4 Aug. 2021. Modified.)

As used herein, "direction" refers to the line or course on which something or someone is moving or is aimed to move; or along which something is pointing or facing. (search "direction" on Merriam-Webster.com. Merriam-Webster, 2021. Web. 4 Aug. 2021. Modified.)

As used herein, a "marking" or "marker" refers to a symbol, letter, lettering, word, phrase, icon, design, diagram, indicator, figure, or combination of these designed, intended, structured, organized, configured, programmed, arranged, or engineered to communication information and/or a message to a user receiving, viewing, or encountering the marking. The marking can include one or more of a tactile signal, a visual signal or indication, an audible signal, and the like. In one embodiment, a marking may comprise a number or set letters, symbols, or words positioned on a surface, structure, or device to convey a desired message or set of information.

As used herein, "blade" refers to a part or structure that resembles the blade of a leaf. A blade can also refer to a planar structure that can be flat or curved and is part of machine, propeller, fan, or turbine, or the like. A blade can also refer to cutting part of an instrument, implement, or tool. (search "blade" on Merriam-Webster.com. Merriam-Webster, 2021. Web. 4 Aug. 2021. Modified.)

As used herein, "tooth" or "teeth" refers to a structure(s) including a natural body part of a person or animal and/or a structure that functions and/or is structured like a similar structure of a person or animal. A tooth can include a base, one or more sides, and an edge. The edge may come to a point or may taper to a sharp edge. The edge or point may serve to tear or cut through or otherwise engage other objects such as food or other materials. A tooth can also refer to a projection resembling or suggesting the tooth of an animal or person in shape, arrangement, or action. (search "tooth" on Merriam-Webster.com. Merriam-Webster, 2021. Web. 4 Aug. 2021. Modified.) A tooth may be made of natural materials such as bone-like material and/or enamel or may be made of a variety of materials including, but not limited to, metal, plastic, ceramic, wood, fiberglass, acrylic, carbon, biocompatible materials, biodegradable materials or the like.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. A surgical saw blade comprising:
a front side, an opposite back side, a top side, an opposite bottom side, a right side, and an opposite left side;
a cutting tooth extending from the back side and having a cutting edge oriented toward one of the right side and the left side, the cutting tooth associated with an aperture through the saw blade between the front and back sides;
wherein the back side is a single direction cutting side and the front, top, bottom, right, and left sides are non-cutting sides;
a saw connection feature near the bottom side, and
one or more markings on the back side, the one or more markings configured to indicate that the back side is a cutting side, wherein the one or more of the markings comprises a direction marker that indicates which direction the single direction cutting side cuts in.

2. The surgical saw blade of claim 1, wherein an aperture width for the aperture is 70% to 115% of a height for the cutting tooth.

3. The surgical saw blade of claim 1, wherein the front side and the opposite back side are the broadest sides of the saw blade.

4. The surgical saw blade of claim 1, wherein the aperture is rectangular and comprises two parallel sides, an arcuate side that connects the two parallel sides and an open side in communication with the cutting edge of the tooth.

5. The surgical saw blade of claim 1, wherein the cutting edge is one of arcuate and straight.

6. The surgical saw blade of claim 1, wherein the cutting edge has a base and extends from the base in a distal direction to a cutting edge that faces the one of the right side and the left side, such that the distal direction is perpendicular to the one of the right side and the left side.

7. An oscillating surgical saw blade comprising:
a front side, an opposite back side, a top side, an opposite bottom side, a right side, and an opposite left side;
a plurality of cutting teeth connected to the back side and each of the cutting teeth having a cutting edge oriented toward a common side of the oscillating saw blade, each of the cutting teeth adjacent to an aperture through the saw blade between the front and back sides;
wherein the front, top, bottom, right, and left sides are non-cutting sides; and
an oscillating surgical saw connection feature near the bottom side, connectable to an oscillating surgical driver of an oscillating surgical saw,
wherein the cutting edge comprises a bevel comprising opposite corner bevels and one or more front bevels.

8. The oscillating surgical saw blade of claim 7, wherein an aperture width for the aperture of each of the plurality of cutting teeth is 70% to 115% of a height for the adjacent of the cutting teeth.

9. The oscillating surgical saw blade of claim 7, wherein the common side comprises one of the right side and the left side.

10. The oscillating surgical saw blade of claim 7, wherein each of the cutting teeth comprises:
a base;
the cutting edge;
a first side between the base and the cutting edge, the first side defining a first slot between the first side and the saw blade;
a second side between the base and the cutting edge, the second side defining a second slot between the second side and the saw blade;
wherein one end of the first slot comprises a first scalloped edge and the opposite end of the first slot connects to the aperture; and
wherein one end of the second slot comprises a second scalloped edge and the opposite end of the second slot connects to the aperture.

11. The oscillating surgical saw blade of claim 10, wherein the first side comprises a first side bevel and second side comprises a second side bevel.

12. The oscillating surgical saw blade of claim 7, wherein the plurality of cutting teeth are organized into a plurality of rows and columns.

13. The oscillating surgical saw blade of claim 12, wherein each row of cutting teeth aligns with apertures of at least one adjacent row of cutting teeth.

14. An oscillating surgical saw blade comprising:
a front side, an opposite back side, a top side, an opposite bottom side, a right side that extends from the top side to the bottom side, and an opposite left side that extends from the top side to the bottom side;
a set of cutting teeth organized into rows and columns;
wherein the cutting teeth extend from the back side and each of the cutting teeth has a base and extends from the base in a distal direction to a cutting edge oriented toward one of the right side and the left side, such that the distal direction is perpendicular to the one of the right side and the left side, each of the cutting teeth associated with a rectangular aperture through the saw blade between the front and back sides; and
an oscillating saw connection feature near the bottom side, connectable to an oscillating surgical driver of an oscillating surgical saw.

15. The oscillating surgical saw blade of claim 14, wherein the cutting teeth in each column are aligned vertically and the cutting teeth in each row are aligned horizontally.

16. The oscillating surgical saw blade of claim 14, wherein each of the cutting teeth comprises:
a base;
the cutting edge;
a first side between the base and the cutting edge, the first side defining a first slot between the first side and the saw blade; and a second side between the base and the cutting edge, the second side defining a second slot between the second side and the saw blade.

17. The oscillating surgical saw blade of claim 16, wherein first side and the second side are parallel to each other.

18. The oscillating surgical saw blade of claim 16, wherein:
- one end of the first slot comprises a first scalloped edge and the opposite end of the first slot connects to the aperture;
- one end of the second slot comprises a second scalloped edge and the opposite end of the second slot connects to the aperture; and
- the first side comprises a first side bevel and second side comprises a second side bevel.

19. The oscillating surgical saw blade of claim 14, wherein each cutting edge comprises a bevel comprising opposite corner bevels and one or more front bevels.

20. The oscillating surgical saw blade of claim 14, wherein an aperture width for each rectangular aperture is 70% to 115% of a height for each of the cutting teeth.

* * * * *